US005830478A

United States Patent [19]
Raso et al.

[11] Patent Number: 5,830,478
[45] Date of Patent: Nov. 3, 1998

[54] METHOD FOR DELIVERING FUNCTIONAL DOMAINS OF DIPHTHERIA TOXIN TO A CELLULAR TARGET

[75] Inventors: Victor A. Raso, Brookline, Mass.; Katherine Sheldon, Nashua, N.H.

[73] Assignee: Boston Biomedical Research Institute, Boston, Mass.

[21] Appl. No.: 472,523

[22] Filed: Jun. 7, 1995

[51] Int. Cl.$^6$ .................................................. A61K 39/395
[52] U.S. Cl. ................................ 424/236.1; 424/136.1; 424/143.1; 424/150.1; 424/178.1; 424/236.1; 424/238.1; 530/387.3; 530/391.7
[58] Field of Search .......................... 424/236.1, 238.1, 424/178.1, 136.1, 143.1, 150.1; 530/387.3, 391.7

[56] References Cited

U.S. PATENT DOCUMENTS

| | | | |
|---|---|---|---|
| 4,664,911 | 5/1987 | Uhr et al. | 424/85 |
| 5,603,931 | 2/1997 | Raso | 424/136.1 |

FOREIGN PATENT DOCUMENTS

| | | |
|---|---|---|
| 0253202 | 1/1988 | European Pat. Off. . |
| WO86/01409 | 5/1985 | WIPO . |
| WO89/11867 | 12/1989 | WIPO . |
| WO91/12023 | 8/1991 | WIPO . |

OTHER PUBLICATIONS

Raso, V., "Immunotargeting Intracellular Compartments", *Anal. Biochem.*, 222:297–304 (1994).

Greenfield, L. et al., "Mutations in Diphtheria Toxin Separate Binding from Entry and Amplify Immunotoxin Selectivity", *Science*, 238:536–538 (1987).

Neville, D.M., Jr. et al., "Enhancement of Immunotoxin Efficacy by Acid–Cleavable Cross–Linking Agents Utilizing Diphtheria Toxin and Toxin Mutants", *J. Biol. Chem.*, 264 (25) :14653–14661 (1989).

Raso, V., "Antibody Mediated Delivery of Cytotoxic Molecules to Antigen Bearing Target Cells", *Immunol. Rev.*, 62:93–117 (1982).

Paik, C.H. et al., "Reduction of Background Activities by Introduction of a Diester Linkage Between Antibody and Chelate in Radioimmunodetection of Tumor", *J. of Nuclear Medicine*, 30 (10) :1693–1701 (1989).

Myers, D.A. et al., Specific Chemicl Cleavage of Diphtheria Toxin with Hydroxylamine, *J. Biol. Chem.*, 263 (32) :17122–17127 (1988).

Murphy, J.R. et al., "Genetic Construction, Expression and Melanoma–Selective Cytotoxicity of Diphtheria Toxin–Related α–Melanocyte–Stimulating Hormone Fusion Protein", *Proc. Natl. Acad. Sci., USA*, 83:8258–8262 (1986).

Bacha, P. et al., "Interleukin 2 Receptor–Targeted Cytotoxicity", *J. Exp. Med.*, 167:612–622 (1988).

Raso, V et al., "Hybrid Antibodies with Dual Specificity for the Delivery of Immunoglobulin–bearing Target Cells", *Cancer Research*, 41:2073–2078 (1981).

Vitetta, E.S., et al., "Synergy of ricin A chain–containing immunotoxins and ricin B chain–containing immunotoxins in in vitro killing of nepolastic human B cells," *Proc. Natl. Acad. Sci. USA* 80:6332–6335.

*Primary Examiner*—James C. Housel
*Assistant Examiner*—Jennifer Shaver
*Attorney, Agent, or Firm*—Hamilton, Brook, Smith & Reynolds, P.C.

[57] ABSTRACT

The method of the present invention employs a hybrid reagent comprising a first portion (i.e., a cell-targeting portion) which binds to cell surfaces coupled to a second portion (i.e., a toxin-binding portion) which binds to, or has bound to it, an endosomally active domain of DT and releases the endosomally active domain of DT in response to the low pH in endosomal vesicles of cells. Thus, the second portion of the hybrid reagent binds an endosomally active domain directly (e.g., an antibody which binds to all or a portion of the T domain of DT) or indirectly (e.g., an antibody which binds to the R domain of a moiety in which the R domain of DT is coupled to the T domain of DT). A second endosomally active domain of DT, which is different from the first endosomally active domain of DT, is delivered to the same endosomal vesicles separately. The independent endosomally active domains of DT are not toxic to cells until they meet within the endosomes. Thus, the therapeutic window of the binary toxin described herein is much greater than current toxin delivery systems, which generally retain collateral toxicity, even when undelivered.

17 Claims, 4 Drawing Sheets

METHOD FOR DELIVERING FUNCTIONAL DOMAINS OF DIPHTHERIA TOXIN TO A CELLULAR TARGET

FUNDING STATEMENT

This work was supported by the National Institutes of Health grants, 5R01 CA49856-05 and 5R01 CA9254-06. Therefore, the U.S. Government has certain rights in the invention.

BACKGROUND

Toxic proteins from plants and bacteria are extremely efficient cytotoxic agents because they can bind to the cell membrane, penetrate into the cytosol and enzymatically inactivate critical elements of protein synthesis, resulting in cell death. Unfortunately, there is little control over which cells are killed by native toxins because the receptor sites to which they bind are common to many cell types.

Typically, the C domain (i.e., the catalytic domain) of toxins such as diphtheria toxin (DT) has been isolated and disulfide linked to antibody or ligand carriers. This strategy eliminates any indiscriminate toxicity due to the R domain (i.e., the binding domain) but yields conjugates with diminished potency and slower kinetics for killing cells. Recently, conjugates have been formed using selectively altered DT which retains the translocation function but have had their R domain binding activity nullified by point mutation, deletion or chemical cleavage (Bacha, P. et al., *J. Exp. Med.*, 167: 612–622 (1988); Greenfield, L., et al., *Science*, 238: 536–539 (1987); Murphy, J. R., et al., *Proc. Natl. Acad. Sci., USA*, 83: 8258–8262 (1986); Myers, D. A., et al., *J. Biol. Chem.*, 263: 17122–17127 (1988)). These toxin conjugates display selectivity and potency on target cells in vitro but have had limited therapeutic success.

Thus, the therapeutic effectiveness of current toxin derivatives is inadequate. A mode of successful targeted toxin therapy is needed to provide increased potency, decreased non-specific interactions and higher penetrability into target tissues.

SUMMARY OF THE INVENTION

The present invention relates to the development of a novel binary toxin system for delivering functional domains of diphtheria toxin to cells based on acid-triggered-toxin release of diphtheria toxin (DT) within endosomes of the cells. The "functional domains" of DT are the catalytic (C) domain, the translocation (T) domain and the receptor (R) domain, and include all or a functional portion of the domains of DT. In particular, functional domains of DT which become active in endosomes (i.e., endosomally active domains of DT) are delivered to cells separately. As defined herein, "endosomally active" domains of DT are the C domain and the T domain.

The method of the present invention employs a hybrid reagent comprising a first portion (i.e., a cell-targeting portion) which binds to cell surfaces coupled to a second portion (i.e., a toxin-binding portion) which binds to, or has bound to it, an endosomally active domain of DT and releases the endosomally active domain of DT in response to the low pH in endosomal vesicles of cells. Thus, the second portion of the hybrid reagent binds an endosomally active domain directly (e.g., an antibody which binds to all or a portion of the T domain of DT) or indirectly (e.g., an antibody which binds to the R domain of a moiety in which the R domain of DT is coupled to the T domain of DT). A second endosomally active domain of DT, which is different from the first endosomally active domain of DT, is delivered to the same endosomal vesicles separately. The independent endosomally active domains of DT are not toxic to cells until they meet within the endosomes. Thus, the therapeutic window of the binary toxin described herein is much greater than current toxin delivery systems, which generally retain collateral toxicity, even when undelivered.

In one embodiment, the present invention relates to a method for delivering functional domains of diphtheria toxin to a cellular target within the cells of a host (e.g., vertebrate, particularly mammalian, such as human) which comprises administering a hybrid reagent -(e.g., antibody, virus, ligand, receptor or molecule) which has a first portion that binds to a surface of cells and a second portion that binds a first endosomally active domain of diphtheria toxin to the host. A second endosomally active domain of diphtheria toxin which is coupled to the R domain of DT is co-administered to the cells of the host. The hybrid reagent binds to the cell surface of the cells and the second endosomally active domain which is coupled to the R domain of the DT binds to DT receptors on the cell surface. The endosomally active domains of DT are endocytosed in the same endosome into the cells, wherein the first endosomally active domain of the diphtheria toxin is released from the second portion of the hybrid molecule and cooperates with the second endosomally active domain of DT resulting in delivery of the endosomally active domains of the DT to the cellular target the said cells. In a further embodiment, the second endosomally active domain of DT is co-administered using a second hybrid reagent which has a first portion that binds to a surface of the cells and a second portion that binds the second endosomally active domain of DT. Thus, as described herein the methods of the present invention can also be used to kill cells by delivering functional domains of DT to a cellular target within the cells of a host.

In another embodiment, the present invention relates to a method for delivering endosomally active domains of DT to a cellular target within the cells of a host which comprises providing a first portion of a hybrid reagent which upon administration to the host at a first pH, binds to a cell surface of the cells with the subsequent pinching off of the surface of the cells to form endosomes having a second and lower pH and containing the hybrid reagent whereby the hybrid reagent is transported to the interior of the cells by endocytosis. A screening analysis is performed to identify an antibody or antibody fragment, which binds all or a functional portion of a first endosomally active domain of DT at the first pH and releases it at a second and lower pH found within endosomes to serve as a second portion of the hybrid reagent. The hybrid reagent which includes the first and second portion is constructed. The hybrid reagent and a second endosomally active domain of DT which is coupled to a R domain of DT are co-administered to the host whereby the constructed hybrid reagent binds to the cell surface and the second endosomally active domain of the diphtheria toxin coupled to the R domain of DT binds to DT receptors on the cell surface, and are endocytosed in the same endosome into said cells. In endosomes which include the hybrid reagent and the second endosomally active domain, the first endosomally active domain of the DT is released from the second portion of the hybrid molecule and cooperates with the second endosomally active domain of DT resulting in delivery of the C domain of the diphtheria toxin to the cellular target within the cells.

In a particular embodiment, the present invention relates to a method for delivering functional domains of DT to a cellular target within the cells of a host as described above, wherein a first endosomally active domain of DT is the C domain and the second endosomally active domain, which is coupled to the R domain of DT, is the T domain. The methods described herein can further comprise the use of a fragment or modified functional domain of DT. For example, a T domain in which the cysteine at 201 in the amino acid sequence of DT is replaced with a different amino acid (e.g., a non-sulfhydryl amino acid such as alanine) can be used in the methods of the present invention.

In another embodiment, a heterodimeric antibody (i.e., acid-triggered or acid-sensitive antibody) system is-used to deliver functional domains of DT to cells. This embodiment comprises providing a first portion of a first hybrid reagent which, upon administration to the host at a first pH, binds to the surface of the cells with the subsequent pinching off of the surface of the cells to form endosomes having a second and lower pH and containing the first hybrid reagent whereby the hybrid reagent is transported to the interior of the cells by endocytosis. A screening analysis is performed to identify an antibody or antibody fragment, which binds all of a portion of a functional domain of the C domain of DT at the first pH and releases it at the second and lower pH found within endosomes, to serve as a second portion of the first hybrid reagent. The first hybrid reagent is constructed.

A first portion of a second hybrid reagent which, upon administration to the host at a first pH, binds to the surface of the cells with the subsequent pinching off of the surface of said cells to form endosomes having a second and lower pH and containing the second hybrid reagent whereby the hybrid reagent is transported to the interior of said cells by endocytosis is provided. The cell surface receptor which the first portion of the second hybrid reagent binds and the first portion of the first hybrid reagent binds can be the same or different, preferably different. A screening analysis is performed to identify an antibody or antibody fragment, which binds all or a functional portion of the T domain of the DT at the first pH and releases it at the second and lower pH found within endosomes to serve as a second portion of the second hybrid reagent. The second hybrid reagent is constructed.

The first hybrid reagent and the second hybrid reagent are co-administered to the host whereby the first hybrid reagent and the second hybrid reagent bind to the surface of the cells, and are endocytosed in the same endosome into the cells. In endosomes which include the first and-second hybrid reagents, the C domain of the DT is released from the second portion of the first hybrid reagent, the T domain of the DT is released from the second portion of the second hybrid reagent, wherein the T domain cooperates with (e.g., facilitates delivery of) the C domain of DT to the cellular target within the cells.

The present invention also relates to a composition for delivering functional domains of DT to cells, comprising a hybrid reagent, which binds to a receptor on the cellular surface and has all or a functional portion of an endosomally active domain of DT bound thereto at a first pH, the hybrid releasing the endosomally active domain of DT at a second and lower pH, and a second endosomally active domain of the DT coupled to the R domain of DT.

In a particular embodiment, the present invention relates to a composition for delivering functional domains of DT to a cell, comprising a hybrid reagent, which binds to a receptor on the cellular surface and has all or a functional portion of a first endosomally active domain of DT bound thereto at a first pH, and a second hybrid reagent, which binds to a receptor on the cellular surface and has all or a functional portion of a second endosomally active domain of DT bound thereto at the first pH, where both hybrids release the cytotoxic domains of DT at a second and lower pH.

The methods and compositions of the present invention provide increased potency, decreased non-specific interactions and higher penetrability of selected toxins into target tissues. The binary toxins described herein provide an extra stringent mode of selectivity that will spare normal tissues and overcome the major impediment of current immunotoxins.

DETAILED DESCRIPTION OF THE INVENTION

The hybrid reagents of the present invention comprise a first portion having an affinity for a cellular surface or target and a second portion having an affinity for an endosomally active domain of diphtheria toxin (e.g., C domain, T domain, functional portions and functional mutations thereof). The hybrid reagents can be administered in vivo where they bind to the external surface of a cell. Once bound to the cell, receptor mediated endocytosis serves to pinch off the surface of the cell forming an endosome, which has a lower pH than either outside or within the rest of the cell. In response to the change in pH within the endosome, the hybrid reagents selectively release the diphtheria toxin (DT) domain.

The first portion of the hybrid reagent has an affinity for a cellular target, such as an antigenic or receptor site on the surface of the cell (e.g., a cell surface receptor or cell surface antigen) or inside a cell (e.g., a receptor or antigen within an endosome). Examples of cellular targets are Ig, c-erbB-2 antigen, common acute lymphoblastic leukemia antigen (CALLA), B1, gp26, Ia, transferrin receptor, EBV transformation antigen, and the receptors for ligands such as IL-2, MSH, insulin, thyroglobulin, LHRH, and NGF. Viral proteins on the surface of infected cells (e.g., HIV-infected T lymphocyte) can also serve as targets for antibody and receptor guided hybrid reagents. The first portion of the hybrid reagent can be, for example, a ligand (e.g., transport proteins such as transferrin, IL-2, LDL), a growth factor (e.g., EGF, PDGF), an antibody, a hormone, a receptor molecule (e.g., recombinant CD4), a virus, or a fragment thereof. Suitable antibodies which can be used in the present invention and are therefore appropriate for the first portion of the hybrid reagent include 7D3, a monoclonal antibody which binds to human transferrin (Griffin et al., *Cancer Res.*, 47: 4266(1987)), C19, directed against the carcinoembryonic antigen (Griffin et al., *J. Biol. Resp. Modif.*, 1: 194

(1982)); 260F9 directed against a breast cancer antigen (Bjorn et al., *Cancer Res.,* 45: 1214 (1985)); 96.5 directed against a melanoma associated antigen (Caselles et al., *In. J Cancer,* 30: 437 (1982)); 45-2D9 directed against an oncogene product (Roth et al., *J. Immunol.,* 136: 2305 (1986)); and J-5 directed against CALLA (Raso et al., *Cancer Res.,* 42: 457 (1982)). In the embodiment in which more than one hybrid reagent is used, the cell surface region to which the first portion of each hybrid binds can be the same or different. Preferably the cell surface region to which the first portion of each hybrid binds is different.

The second portion of the hybrid reagent is an antibody or an antibody fragment that has an affinity for an endosomally active domain of DT at a first pH and releases the endosomally active domain of DT at a second and lower pH. The first pH is about physiologic pH (e.g., 6.5 to 7.5), which is the first pH the hybrid reagent encounters outside the cells containing the cellular target or upon in vivo administration to the host. Thus, the antibody or antibody fragment has an affinity for an acid-sensitive site of an endosomally active domain of DT. That is, an acid sensitive site is one which changes conformation at a lower pH, such as that found in endosomes (e.g., about 4.5 to about 5.5). Suitable antibodies which can be used to bind acid-sensitive sites of DT include D4B7 (i.e., a monoclonal antibody which binds a portion of the C domain of DT), D5D5 (i.e., a monoclonal antibody that binds a potion of the T domain), D5E8, D1F3, D6B3 and D1D5.

Endosomally active domains of DT can also be delivered to a cell using the R domain of DT (e.g., an endosomally active domain-R moiety). For example, an endosomally active domain (i.e., C domain, T domain) of DT can be coupled to the R domain of DT and, thus, enter the cell via native DT receptors. For example, as described in Example 1, the translocation domain of a translocation-receptor moiety enters the cell via the native DT receptors. Linking of the endosomally active domain to the R domain of DT can be performed using a variety of techniques, such as genetic engineering as described in Example 1.

Figure 1:
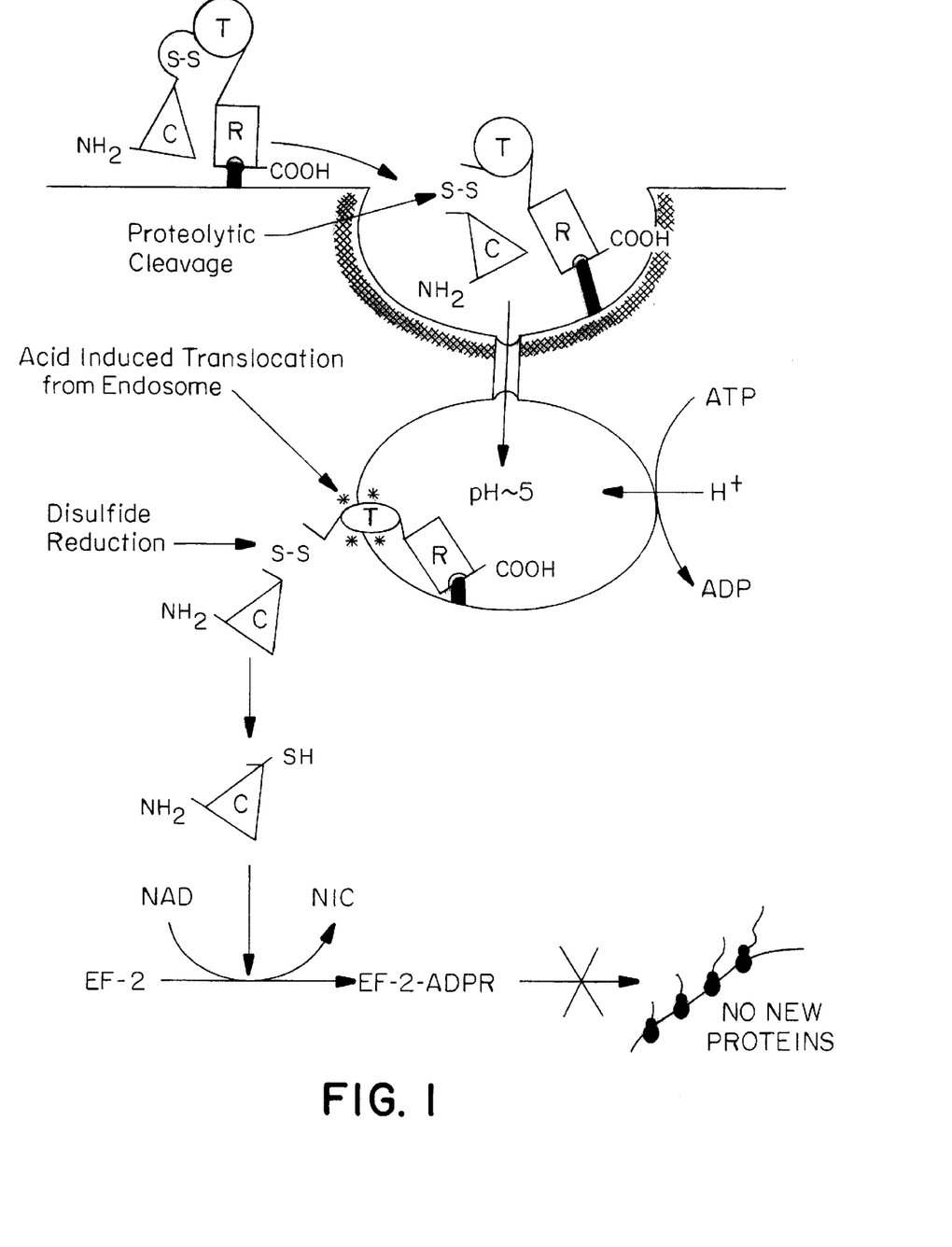
FIG. 1 is a schematic diagram depicting the delivery of the diphtheria toxin (DT) to a cell by receptor mediated endocytosis.
Figure 2:
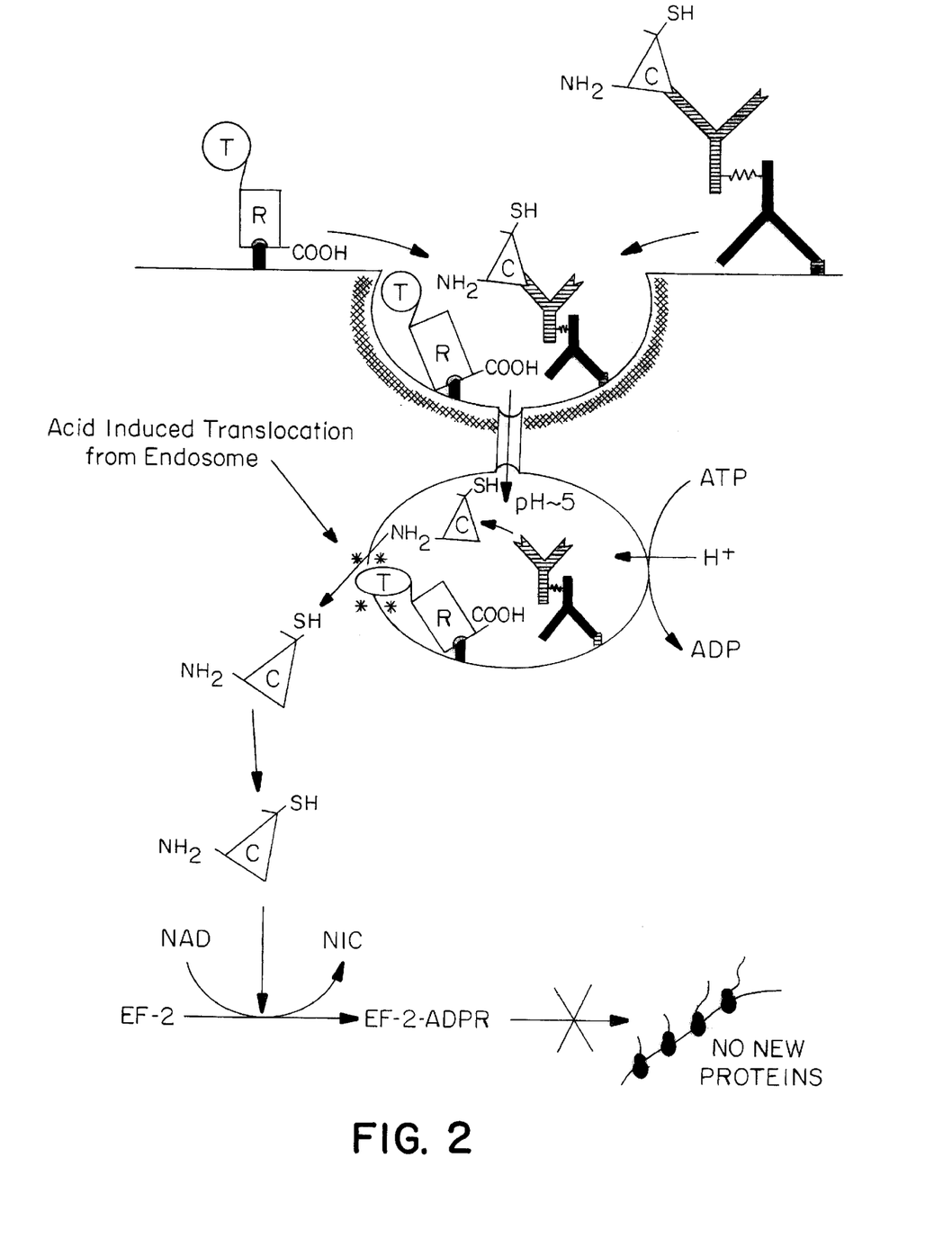
FIG. 2 is a schematic diagram depicting delivery of the C domain of the DT from a hybrid reagent and delivery of a translocation-receptor (T-R) domain of the DT by receptor mediated endocytosis.

DT is a single chain polypeptide comprised of 535 amino acid residues. Its crystal structure depicts three physical domains which correlate closely with its three functional activities, receptor binding (R), translocating (T) and catalytic (C) (FIG. 1). The C domain comprises amino acids 1–193, the T domain comprises amino acids 194–386 and the R domain comprises amino acids 387–535. The cell-surface receptor used by DT is an integral membrane protein that has been cloned and identified as a heparin-binding EGF-like growth factor precursor.

Proteolytic cleavage of DT may occur prior to or following its entry into cells but the enzyme that is responsible has not yet been identified. The site of attack, a protease sensitive 16-amino acid loop formed by a disulfide bond linking Cys 186 to Cys 201, joins the C and T domains of DT. Proteolysis makes the C domain enzymatically active and renders it competent for passage through membranes.

Receptor-toxin complexes on the plasma membrane quickly accumulate in clathrin-coated pits. Within –1 minute these complexes move into endosomes which have an internal pH ranging between about pH 6 to about pH 5. Endosomal pH is decreased by a vacuolar $H^+$-ATPase (V-ATPase) that resides in its membrane. This enzyme complex has evolved in eukaryotic cells to function exclusively as an ATP-dependent proton pump for acidifying the lumenal space.

In response to low pH, DT is triggered to undergo a conformational change, injecting its poisonous C domain into the cytosol. Analysis of the crystal structure of DT has provided an indication of how this translocation occurs. The T domain contains two closely spaced, parallel loops, which have six negatively charged aspartate and glutamate residues. These loops are hydrophilic at pH 7 and shield four hydrophobic helices buried beneath them. At pH 5 however, the carboxylate side chains become protonated, allowing the neutralized loops and newly exposed apolar helices to insert into the membrane.

The mechanism by which these inserted T helices mediate translocation of the C domain across endosomal membranes is not yet known. Whether this proceeds while the two moieties are disulfide-linked or requires their separation first, remains to be determined.

The C domain must be reductively detached from the rest of the molecule to acquire enzymatic activity, but it is not clear if this happens prior to, during, or after translocation into the cytosol. The protease-cleaved and reduced C domain now functions as a fully active enzyme, which inactivates elongation factor 2 (EF-2) by selectively ADP-ribosylating its unique diphthamide residue. Once the cell's supply of EF-2 is depleted, it can no longer synthesize protein and enters an apoptotic mode of cell death.

Domains of DT for use in the present invention are the C domain, the T domain, the R domain, and include functional mutations (i.e., modified) and functional portions thereof (i.e., truncated). Examples of truncated domains of DT which can be used in the present invention are described in Example 5. Portions of the C domain which can be used in the present invention include for example, $DT_{1-190}$ and $DT_{1-193}$. Portions of the T domain for use in the present invention include for example, $T_{194-370}$ and $T_{201-370}$. Preferably, the C domain or the T domain for use in the present invention is modified so that they are precluded from any covalent interaction. For example, the cysteine at position 201 of the DT amino acid sequence the T domain region, is replaced with a different amino acid (e.g., a non-sulfhydryl amino acid such as alanine or valine). Further, as defined herein, an "endosomally active domain" of DT refers to the C domain or the T domain of DT.

The terms "functional portion", "fragment", "mutated portion" (e.g., modified), or "derivative" refer to the portion of the DT domain, or the portion of the DT domain sequence which encodes the DT domain protein, that is of sufficient size and sequences to have the desired function (e.g., catalytic, translocation or receptor binding functions). Functional equivalents or derivatives of the DT domains include modified DT domains such that the resulting DT domain has the same or similar activity as the natural or native DT domain, and/or nucleic acid sequences which, for example, through the degeneracy of the genetic code encode a similar peptide gene product as the DT domain and/or have the same DT domain as described herein. For example, a functional equivalent of a DT domain can contain a "silent" codon or one or more amino acid substitutions, deletions or additions (e.g., substitution of one acidic amino acid for another acidic amino acid; substitution of one codon encoding a hydrophobic amino acid for another codon encoding the same or a different hydrophobic amino acid). See Ausubel, F. M., *Current Protocols in Molecular Biology,* Greene Publishing Assoc. and Wiley-Interscience 1989.

The DT domains can be obtained from a suitable source for use in the present invention. For example, the DT domains can be purified from natural sources (e.g., bacterial), produced by chemical synthesis or produced by recombinant DNA techniques as described in Example 1.

Antibodies for use in the present invention bind acid-sensitive sites of DT either directly (e.g., an antibody which binds to all or a portion of an endosomally active domain of DT, such as T) or indirectly (an antibody which binds to an R domain of a moiety in which the R domain of DT is coupled to the T domain of DT) and can be identified using a variety of methods. For example, the method described in U.S. Ser. No. 07/998,754 ('998), which is hereby incorporated by reference, can be used to identify antibodies which bind acid-sensitive sites of the DT. Briefly, as described in '998, antibodies which bind a domain of DT are prepared using known methods. Clone supernatants are then assayed for the ability to bind the DT domain at the first pH selected. Clones testing positive for binding ability are screened to isolate those that release the DT domain at a second selected lower pH. Thus, for example, antibodies that bind the C domain at physiologic pH (i.e., about 6.5 to about 7.5) can be-tested to isolate clones that release the C domain at acidic pH (about 4.5 to about 5.5).

The antibodies of the present invention can be polyclonal or monoclonal, and the term antibody is intended to encompass both polyclonal and monoclonal antibodies. Antibodies of the present invention are raised against an appropriate region or epitope of a region of a cell surface or an appropriate domain of the DT, portions thereof, or synthetic DT molecules, such as synthetic DT peptides. In addition, cells which express DT, such as transfected cells, can be used as immunogens or in a screen for antibody which binds DT. See for example, Chuntharapai et al., *J. Immunol.* 152: 1783–1789 (1994)).

Preparation of immunizing antigen, and polyclonal and monoclonal antibody production can be performed using any suitable technique. A variety of methods have been described, such as the use of combinatorial libraries as described in Marks, J., et al., *J. Mol. Biol.*, 222: 581–597 (1991). Also see e.g., Kohler et al., *Nature*, 256: 495–497 (1975) and *Eur. J. Immunol.* 6: 511–519 (1976); Milstein et al., *Nature* 266: 550–552 (1977); Koprowski et al., U.S. Pat. No. 4,172,124; Harlow, E. and D. Lane, 1988, *Antibodies: A Laboratory Manual,* (Cold Spring Harbor Laboratory: Cold Spring Harbor, N.Y.); *Current Protocols In Molecular Biology,* Vol. 2 (Supplement 27, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line such as SP2/0, NS1) with antibody producing cells. The antibody producing cell, preferably those of the spleen or lymph nodes, are obtained from animals immunized with the antigen of interest. The fused cells (hybridomas) are isolated using selective culture conditions, and cloned by limiting dilution. Cells which produce antibodies with the desired specificity-are selected by a suitable assay (e.g., ELISA).

Single chain antibodies, and chimeric, humanized or primatized (CDR-grafted) antibodies, as well as chimeric or CDR-grafted single chain antibodies, comprising portions derived from different species, are also encompassed by the present invention and the term "antibody".

In addition, functional fragments of antibodies, including fragments of chimeric, humanized, primatized or single chain antibodies, can also be produced. Functional fragments of foregoing antibodies retain at least one binding function and/or modulation function of the full-length antibody from which they are derived. For example, antibody fragments capable of binding to a DT domain or portion thereof, including, but not limited to, Fv, Fab, Fab' and F(ab')$_2$ fragments, are encompassed by the invention. Such fragments can be produced by enzymatic cleavage, by recombinant techniques or by combinatorial library techniques (Marks, J., et al., *J. Mol. Biol.*, 222: 581–597 (1991). For instance, papain or pepsin cleavage can generate Fab or F(ab')$_2$ fragments, respectively. Alternatively, antibodies can be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain.

Anti-idiotypic antibodies are also provided. Anti-idiotypic antibodies recognize antigenic determinants associated with the antigen-binding site of another antibody. Anti-idiotypic antibodies can be prepared against second antibody by immunizing an animal of the same species, and preferably of the same strain, as the animal used to produce the second antibody. See e.g., U.S. Pat. No. 4,699,880. Anti-idiotypic (i.e., Anti-Id) antibody can itself be used to raise an anti-idiotypic antibody (i.e., Anti-anti-Id). Such an antibody can be similar or identical in specificity to the original immunizing antibody.

Single chain, and chimeric, humanized or primatized (CDR-grafted), as well as chimeric or CDR-grafted single chain anti-idiotypic antibodies can be prepared, and are encompassed by the term anti-idiotypic antibody. Antibody fragments of such antibodies can also be prepared.

The hybrid reagents of the present invention can be produced by joining together the first and second portions using known techniques (e.g., chemical coupling, cell fusion, or genetic engineering techniques). The hybrid reagents are preferably made by chemically coupling the two portions together. For example, a disulfide linkage using N-succinimidyl-3-(2-pyridyldithio) propionate (SPDP) as the crosslinking agent can be used (Raso et al., *NATO Advanced Studies Institute,* 82: 119–138 (1984).

When the first and second portions of the hybrid reagents are antibodies two whole parental antibodies may be joined together to produce the hybrid reagent. A variety of crosslinking agents such as protein A, carbodiimide and SPDP can be used to link the whole parental antibodies (Kranz et al., *Proc. Natl. Acad. Sci., USA,* 78: 587 (1981); U.S. Pat. No. 4,474,893).

In addition, the various portions of these antibodies can be joined together chemically by conventional techniques, or can be prepared as a contiguous protein using genetic engineering techniques. See, for example, Paulus, H., U.S. Pat. No. 4,444,878. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M.S. et al., European Patent No. 0,194,276 B1; Winter, U.S. Pat. No. 5,225,539; and Winter, European Patent No. 0,239,400 B1. See also, Newman, R. et al., *BioTechnology,* 10: 1455–1460 (1992), regarding primatized antibody, and Ladner et al., U.S. Pat. No. 4,946,778 and Bird, R. E. et al., *Science,* 242: 423–426 (1988)) regarding single chain antibodies.

Thus, the parental antibodies can be produced by chemically joining parental antibody fragments containing a sufficient portion of the antigen binding region to allow the fragment to bind to its respective antigen (Nisonoff et al., *Arch. Biochem. Biophys.,* 93: 460–467 (1961); Raso et al., *Cancer Res.,* 41: 2073–2078 (1981). The two types of parental antibodies can then be separately digested with pepsin. Bispecific F(ab')₂ molecules can be used as described in Example 1.

The hybrid antibodies can also be produced using cell fusion techniques as described in U.S. Pat. No. 4,474,893. In this patent, hybridoma cells which secrete the parental antibodies are fused together to form quadromas or trioma cells. The cells secrete bi-specific antibodies possessing the antigen binding region of both parental antibodies.

In addition, the hybrid antibodies can be produced using genetic engineering techniques. For example, DNA encoding the heavy and light chain variable regions of each of the parental antibodies are introduced into an appropriate host cell, preferably a lymphoid cell (e.g., a myeloma cell). The transformed cell can then synthesize, assemble and secrete the hybrid antibody.

The compositions described herein (i.e., hybrid reagents and moieties) can be administered to a host in a variety of ways. The routes of administration include intradermal, transdermal (e.g., slow release polymers), intramuscular, intraperitoneal, intravenous, subcutaneous, oral, epidural and intranasal routes. Any other convenient route of administration can be used, for example, infusion or bolus injection, or absorption through epithelial or mucocutaneous linings. In addition, the reagents and moieties of the invention can be administered with other components or biologically active agents, such as pharmaceutically acceptable surfactants (e.g., glycerides), excipients (e.g., lactose), carriers, diluents and vehicles. If desired, certain sweetening, flavoring and/or coloring agents can also be added. The hybrid reagents and moieties can be administered prophylactically or therapeutically to a host and can result in amelioration of, or elimination of a disease state (e.g., cancer).

The administration of the compositions described herein can occur simultaneously or sequentially in time. For example, with sequential administration, a hybrid reagent which binds to transferrin receptors and which has an endosomally active domain (e.g., C domain or T domain) of DT bound thereto can be administered first, allowing sufficient time for the hybrid reagent to localize on the cell surface. The vacant toxin binding sites on the hybrid-bound cells can then be filled by subsequent administration of a toxic moiety (e.g., C- or T-R moiety). In addition, a hybrid reagent in which the first portion binds to cell surface receptors and the second portion binds to an endosomally active domain of DT, can be administered to a host wherein the endosomally active domain is not bound to the second domain of the hybrid reagent. The endosomally active domain of DT to which the second portion of hybrid reagent binds can be administered to the host either before or after the administration of the hybrid reagent. In this instance, binding of the endosomally active domain to the hybrid reagent can occur in vivo. Thus, the term "co-administration" is used herein to mean that the compositions described herein will be administered at times that will achieve significant concentrations in the host for allowing delivery of the endosomally active domains of DT separately to cells, whereby the compositions are endocytosed into the same endosome and cooperate to deliver the endosomally active domains to the cellular target within the cell.

The present invention described herein can be used therapeutically to selectively kill cells having particular cell surface characteristics. Upon administration to a host, genetically engineered catalytic C moiety can be delivered to transferrin receptors on a cell using the hybrid reagents described herein, while a genetically engineered modified translocation-receptor binding (TR) moiety can be delivered to natural DT receptors on the membrane. The independent C and T-R domains cooperate when they meet within the endosome and toxicity results. The therapeutic window is much greater since neither C nor T-R is toxic until they meet inside the target cell. This contrasts with covalently-linked whole toxin, C-T-R or even the C-T molecule which retains some collateral toxicity, even when undelivered.

In addition, a hybrid reagent comprising a first portion having an affinity for an antigen associated with breast cancer and a second portion having an affinity for the C domain of DT, and a genetically engineered T-R moiety can be administered to a host. The C domain is delivered to the breast cancer receptors on a cell and the T domain is delivered to natural DT receptors on a cell, and only cells expressing both receptors will endocytose both cytotoxic portions of the DT in the same endosome. Thus, the administration of the C domain of DT with, but separate from, the T domain of DT results in selective killing of breast cancer cells (i.e., cells expressing the c-erbB-2 antigen and the DT receptor).

A dual target antigen, binary toxin, delivery system has been demonstrated herein. Targeting separated catalytic C domain and the binding/translocation T-R moiety to different cell receptors show that these molecules were individually conveyed into the same acidic endosomal compartment where translocation through the membrane occurred and caused death. Once internalized as separate entities, the unconnected T-R fragment facilitated translocation of the free C moiety through the endosomal membrane in an acid-dependent manner and caused cell death. In addition, separate acid-triggered bispecific antibodies that mediate toxin delivery into target cells by binding to either the C, T or R domains of the DT molecule plus any chosen membrane antigen can be used therapeutically.

Figure 3:
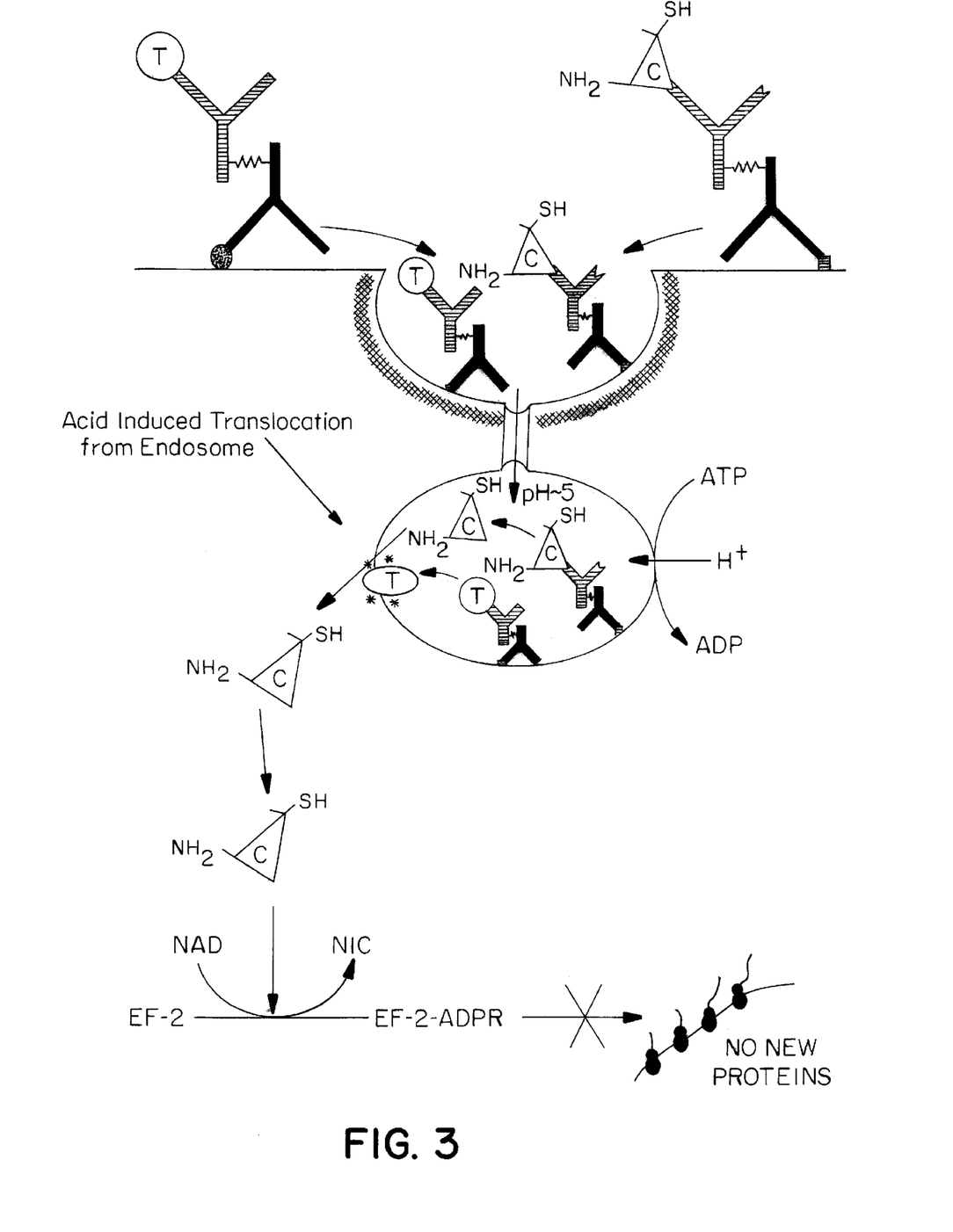
FIG. 3 is a schematic diagram depicting delivery of the C domain of the DT from a first hybrid reagent and delivery of the T domain of the DT from a second hybrid reagent by receptor mediated endocytosis.

Thus, a novel non-covalent heterodimeric antibody system based upon acid-triggered toxin release has been developed for delivery of DT into cells. Binary toxin delivery is important for attaining very stringent selectivity since cells which possess two chosen antigens on their surface (e.g., breast cancer cells with c-erbB-2 and epidermal growth factor receptors) would internalize both components and allow them to cooperate to form active toxin. This can be achieved, for example, by deploying two bispecific antibodies having distinct receptor-targeting and toxin-binding activities (FIG. 3). In this case the genetically engineered T domain and C moiety are independently delivered to different targets on the same cell so that translocation into the cytosol and cell death occur only after they meet within the acidic endosomes of the cell. If the delivered T molecule acts to make the endosome generally permeable then the alternative toxic molecules may be co-delivered in place of the DT catalytic C domain (e.g., ricin A chain).

A binary mode of delivery of the modified toxin-components is important because it can provide increased potency, decreased non-specific interactions and higher penetrability into target tissues. Bipartite targeting of separated C and T moieties to malignant cells will impart an extra stringent mode of selectively that will spare normal tissues and overcome the major impediment of current immunotoxins, dose-limiting nonspecific toxicity. This new binary toxin strategy will result in greatly improved analytical agents and provide the increases in therapeutic advantage needed for successful targeted toxin therapy.

Based on the experiments described herein, it is believed that the present invention can be used with other toxins which have multiple domains that become endosomally active and result in toxicity to a cell. In addition, the domains of the toxin must be able to be separately transported into a cell. Thus, other toxins for use in the present invention must undergo a pH dependent conformational change wherein the pH change is a pH drop from physiological pH to endosomal pH. For example, the shigella toxin may be used in the methods of the present invention.

The invention is further illustrated by the following examples.

EXEMPLIFICATION

EXAMPLE 1

Use of the Binary Toxin to Kill Human Leukemia CEM Cells

A genetically engineered catalytic domain (C) of diphtheria toxin (DT) comprised of amino acids 1–190 was prepared. A genetically engineered translocation/receptor binding domains (TR) of DT comprised of amino acids 201–535 was also prepared. A covalently-linked bispecific (hybrid) antibody molecule comprised of the D4B7 acid-sensitive monoclonal antibody that binds $C_{190}$ at neutral pH and releases it at low pH plus the cell-targeting 7D3 monoclonal antibody that binds to human transferrin receptors on the leukemia CEM cells was prepared.

Human leukemia CEM cells maintained in tissue culture were resuspended in leucine-free minimal essential medium and 200 μl was delivered to the wells of a microtitre plate. Dilutions of each of the three component agents ($C_{190}$, 4B7/7D3, and $TR_{201-535}$) were added either alone or in combination as designated and the plates were cultured for 18 hours at 37° C. in a 5% $CO_2$ incubator. These cells were then pulse labeled with $^3$H-leucine for 30 minutes, collected on glass fiber filter discs and the level of radioactivity incorporated into protein measured in a liquid scintillation counter. The reduction in protein synthesis compared to untreated cells represents the percentage of cells killed by the combination of agents.

As shown in part 1 of Table 1, minimal cell death was achieved when different amounts of $C_{190}$ were delivered into cells by the 4B7/7D3 bispecific antibody. Part 2 of Table 1 shows that while minimal cell death is achieved when 2 μg of $C_{190}$ plus 2 μg of $TR_{201-535}$ is added to cells in the absence of the 4B7/7D3 bispecific antibody, the level rises to 97.8% cells killed when all three components are present. This result demonstrates that the lethal action is dependent upon delivery of both $C_{190}$ into cells via the transferrin receptor and delivery of $TR_{201-535}$ into cells by the DT receptor.

Part 3 of the Table 1 shows the dependence of the % of cells killed upon adding varying amounts of $TR_{201-535}$ to a constant amount of 4B7/7D3 delivered $C_{190}$ (0.2 μg).

Part 4 of Table 1 shows the dependence of the % of cells killed upon adding varying amounts of $TR_{201-535}$ to a lower constant amount of 4B7/7D3 delivered $C_{190}$ (0.02 μg).

Part 5 of Table 1 shows the dependence of the % of cells killed upon varying amounts of 4B7/7D3 delivered $C_{190}$ added to a constant amount of $TR_{201-535}$ (1 μg).

TABLE 1

Use of Binary Toxin to Kill Human Leukemia CEM Cells

| | AGENTS ADDED | | % CELLS KILLED |
|---|---|---|---|
| 1 | $C_{190}$(0.4 μg) + 4B7/7D3 | | 32.6 |
| | $C_{190}$(0.2 μg) + 4B7/7D3 | | 25.9 |
| | $C_{190}$(0.1 μg) + 4B7/7D3 | | 30.0 |
| | $C_{190}$(0.04 μg) + 4B7/7D3 | | 27.0 |
| 2 | $C_{190}$(0.2 μg) | +$TR_{201-535}$(2 μg) | 23.6 |
| | $C_{190}$(0.2 μg) + 4B7/7D3 | +$TR_{201-535}$(2 μg) | 97.8 |
| 3 | $C_{190}$(0.2 μg) + 4B7/7D3 | | 21.0 |
| | $C_{190}$(0.2 μg) + 4B7/7D3 | +$TR_{201-535}$(2 μg) | 98.2 |
| | $C_{190}$(0.2 μg) + 4B7/7D3 | +$TR_{201-535}$(1 μg) | 95.7 |
| | $C_{190}$(0.2 μg) + 4B7/7D3 | +$TR_{201-535}$(0.5 μg) | 94.2 |
| | $C_{190}$(0.2 μg) + 4B7/7D3 | +$TR_{201-535}$(0.2 μg) | 82.9 |
| | $C_{190}$(0.2 μg) + 4B7/7D3 | +$TR_{201-535}$(0.1 μg) | 65.9 |
| 4 | $C_{190}$(0.02 μg) + 4B7/7D3 | | 20.3 |
| | $C_{190}$(0.02 μg) + 4B7/7D3 | +$TR_{201-535}$(2 μg) | 95.3 |
| | $C_{190}$(0.02 μg) + 4B7/7D3 | +$TR_{201-535}$(1 μg) | 91.7 |
| | $C_{190}$(0.02 μg) + 4B7/7D3 | +$TR_{201-535}$(0.5 μg) | 79.6 |
| | $C_{190}$(0.02 μg) + 4B7/7D3 | +$TR_{201-535}$(0.2 μg) | 52.6 |
| | $C_{190}$(0.02 μg) + 4B7/7D3 | +$TR_{201-535}$(0.1 μg) | 45.4 |
| 5 | $C_{190}$(0.4 μg) + 4B7/7D3 | +$TR_{201-535}$(1 μg) | 97.4 |
| | $C_{190}$(0.2 μg) + 4B7/7D3 | +$TR_{201-535}$(1 μg) | 98.3 |
| | $C_{190}$(0.1 μg) + 4B7/7D3 | +$TR_{201-535}$(1 μg) | 98.7 |
| | $C_{190}$(0.04 μg) + 4B7/7D3 | +$TR_{201-535}$(1 μg) | 94.2 |
| | $C_{190}$(0.02 μg) + 4B7/7D3 | +$TR_{201-535}$(1 μg) | 67.2 |
| | $C_{190}$(0.01 μg) + 4B7/7D3 | +$TR_{201-535}$(1 μg) | 31.1 |

EXAMPLE 2

The Binary Toxin Requires a Low pH in the Endosome to Kill the Target Cell

The protocol for this experiment is essentially as described in Example 1. As previously demonstrated, under normal cellular conditions the combined action of $C_{190}$ delivered by the 4B7/7D3 bispecific antibody and $TR_{201-535}$ killed 90.5% of the cells. However, as shown in Table 2, this effect was totally blocked and only 3% of cells were killed when 10 mM $NH_4Cl$ was included in the culture medium to raise the pH in the endosomal compartment of the cell. This result clearly shows that the low pH inside the cell is required for release of $C_{190}$ from the 4B7/7D3 bispecific antibody and for the translocation activity of $TR_{201-535}$.

TABLE 2

Binary Toxin requires a Low pH in the Endosome to Kill the Target Cell

| AGENTS ADDED | | % CELLS KILLED |
|---|---|---|
| $C_{190}$(0.04 μg) + 4B7/7D3 +$TR_{201-535}$(2 μg) | | 90.5 |
| $C_{190}$(0.04 μg) + 4B7/7D3 +$Tr_{201-535}$(2 μg) | +$NHY_4Cl$ | 3.0 |

EXAMPLE 3

Comparison of the Delivery of the Binary Toxin Via a Bispecific Antibody Versus a Covalently Linked Binary Toxin The protocol for this experiment is essentially the same as described in Example 1. 4B7/7D3 (Fab')$_2$ is a covalently-linked bispecific (hybrid) antibody molecule comprised of the Fab' fragment of the D4B7 acid-sensitive monoclonal antibody that binds $C_{190}$ at neutral pH and releases it at low pH, disulfide-coupled to the Fab' fragment of the cell-targeting 7D3 monoclonal antibody that binds to human transferrin receptors on the CEM cells. 7D3(Fab')ssC$_{190}$ is the C$_{190}$ genetically engineered catalytic domain of DT disulfide-linked to the Fab' fragment of the cell-targeting 7D3 monoclonal antibody that binds to human transferrin receptors on the CEM cells.

The results, shown in Table 3, indicate that the 4B7/7D3 (Fab')$_2$ delivered C$_{190}$ by itself provides minimal killing of the target cells. However, this action is greatly enhanced when TR$_{201-535}$ simultaneously enters these cells with the result that 98.3% of the target cells are killed. When C$_{190}$ was delivered into the cells as part of a 7D3 (Fab')ssC$_{190}$ covalently linked conjugate it also produced minimal killing of the target cells. In contrast, no significant enhancement for killing cells was achieved by the addition of the TR$_{201-535}$ translocation/receptor binding domains. This finding strongly indicates that for C$_{190}$ and TR$_{201-535}$ cooperate to provide cytotoxicity within the cell they must both be free. This is the case when C$_{190}$ is reversibly bound to and delivered by the acid-releasable bispecific 4B7/7D3 (Fab')$_2$ but it is not the case when it is covalently tethered to the 7D3 (Fab').

TABLE 3

Comparison of the Delivery of the Binary Toxin Via a Bispecific Antibody Versus a Covalently linked Binary Toxin

| AGENTS ADDED | | % CELLS KILLED |
|---|---|---|
| C$_{190}$(1 μg) + 4B7/7D3(Fab')$_2$ | | 40.5 |
| C$_{190}$(1 μg) + 4B7/7D3(Fab')$_2$ | +TR$_{201-535}$(1 μg) | 98.3 |
| 7D3(Fab')ssC$_{190}$(4 μg) | | 49.2 |
| 7D3(Fab')ssC$_{190}$(4 μg) | +TR$_{201-535}$(1 μg) | 64.2 |

EXAMPLE 4

Binary Toxins are Non-Toxic in DT Sensitive Hamsters

Figure 4:
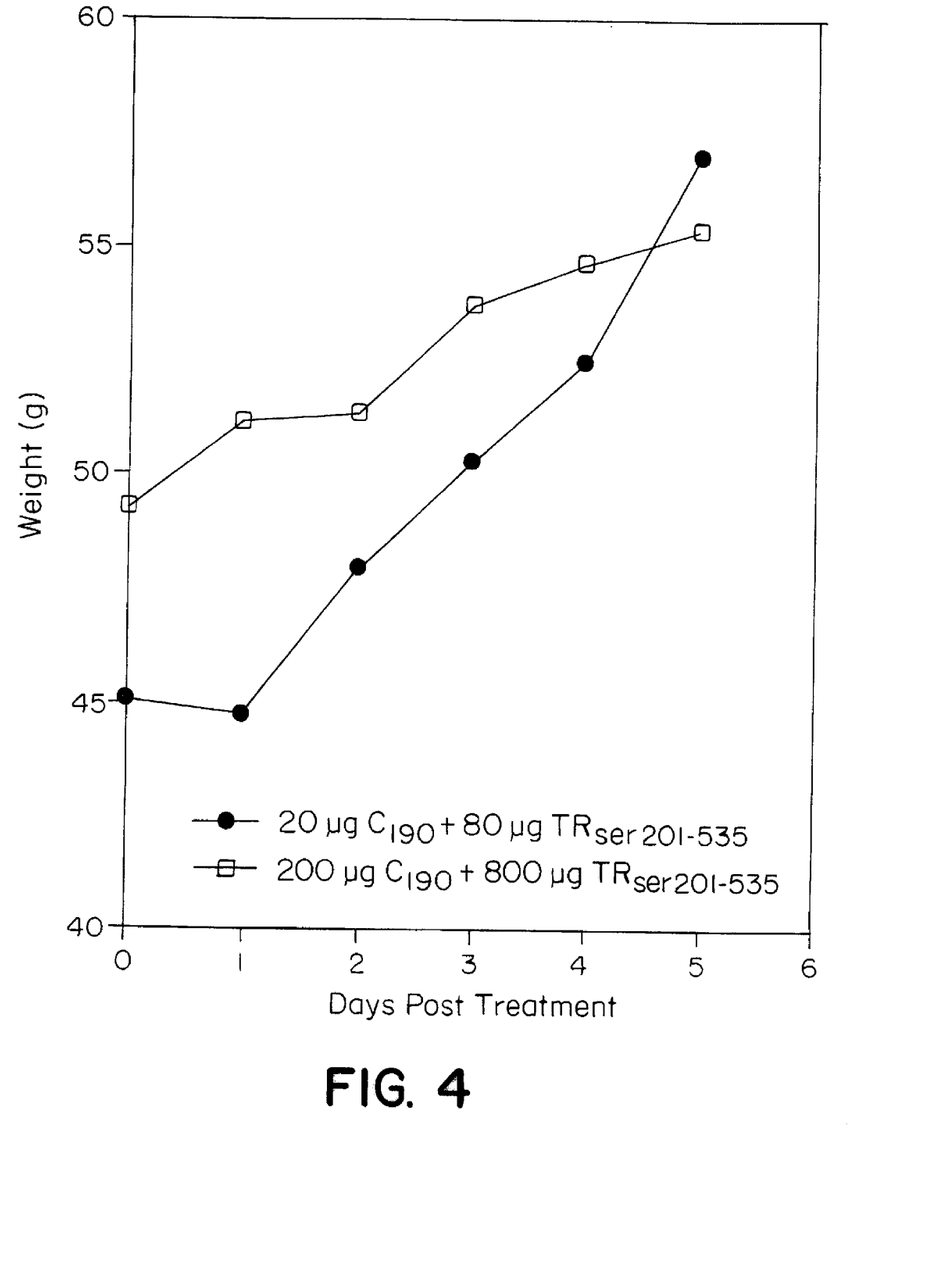
FIG. 4 is a graph of days post treatment versus weight of hamsters injected with a mixture containing either 20 µg $C_{190}$ and 80 µg $TR_{201-535}$ or 200 µg $C_{190}$ and 800 µg $TR_{201-535}$.

Hamsters are acutely sensitive to the toxic effects of DT and were therefore used to test for any potential side effects of C$_{190}$ plus TR$_{201-535}$. Separate hamsters were injected i.p. with a mixture containing either 20 μg C$_{190}$ and 80 μg TR$_{201-535}$ or 200 μg C$_{190}$ and 800 μg TR$_{201-535}$. The weights of these animals was then monitored over the course of several days. As shown in FIG. 4, no toxicity was apparent since no weight loss was detected. Instead, the weight of the hamsters increased in a normal manner. They lived for several weeks before the experiment was ended. In contrast, a litter mate which was injected i.p. with only 1 μg of native DT died in less than 18 hours. These results show that the two components of the binary toxin have no capacity to form active DT since they showed no signs of toxicity even though the dose of C$_{190}$ plus TR$_{201-535}$ was at a 600-fold molar excess over the 1 μg lethal dose of native DT.

EXAMPLE 5

Truncated Diphtheria Toxins

Experiments were performed as described in Example 1, except truncated domains of DT were used. The results are shown in Table 4.

TABLE IV

| C-MUTANTS | PERCENT OF CELLS KILLED |
|---|---|
| C$_{181}$-T$_{370}$(10$^{-8}$M) | 7.3 |
| C$_{182}$-T$_{370}$(10$^{-8}$M) | 85.9 |

TABLE IV-continued

| C-MUTANTS | PERCENT OF CELLS KILLED |
|---|---|
| C$_{183}$-T$_{370}$(10$^{-8}$M) | 89.2 |
| C$_{186}$-T$_{370}$(10$^{-8}$M) | 99.5 |
| C$_{190}$-T$_{370}$(10$^{-8}$M) | 99.0 |
| C$_{190}$-T$_{364}$(10$^{-8}$M) | 18.1 |
| C$_{190}$-T$_{365}$(10$^{-8}$M) | 34.4 |
| C$_{190}$-T$_{370}$(10$^{-8}$M) | 98.8 |

Equivalents

Those skilled in the art will know, or be able to ascertain using no more than routine experimentation, many equivalents to the specific embodiments of the invention described herein. These and all other equivalents are intended to be encompassed by the following claims.

We claim:

1. A method for delivering functional domains of diphtheria toxin to a cellular target within the cells of a host, comprising:

a) administering to said host a hybrid reagent which has a first portion that binds to a surface of said cells and a second portion that is reversibly bound to a first endosomally active domain of diphtheria toxin wherein said first portion is joined to said second portion; and b) co-administering to said host a free second reagent comprising a second endosomally active domain of diphtheria toxin coupled to a receptor domain of diphtheria toxin to said host;

wherein the hybrid reagent is not joined to the second endosomally active domain and the second reagent is not joined to the first endosomally active domain whereby said hybrid reagent binds to the cell surface of said cells and said second endosomally active domain coupled to the receptor domain of the diphtheria toxin binds to diphtheria toxin receptors on the cell surface, and are endocytosed in the same endosome into said cells, wherein said first endosomally active domain of the diphtheria toxin is released from said second portion of the hybrid molecule and cooperates with the second endosomally active domain of diphtheria toxin to form active diphtheria toxin resulting in delivery of said endosomally active domains of the diphtheria toxin into the cellular target within said cells.

2. The method of claim 1 wherein the first endosomally active domain is the C domain of diphtheria toxin and the second endosomally active domain is the T domain of diphtheria toxin.

3. The method of claim 2 wherein the C domain of the diphtheria toxin is selected from the group consisting of: C$_{1-190}$ and C$_{1-193}$.

4. The method of claim 1 wherein the first portion binds to a cell surface receptor.

5. The method of claim 1 further comprising the steps of:

a) providing a first portion of a hybrid reagent which, upon administration to the host at a first pH, binds to a cell surface of said cells with the subsequent pinching off of the surface of said cells to form endosomes having a second and lower pH and containing said hybrid reagent whereby the hybrid reagent is transported to the interior of said cells by endocytosis;

b) screening antibodies or antibody fragments which bind all or a functional portion of a first endosomally active domain of diphtheria toxin to determine which of said antibodies or antibody fragments bind said first endosomally active domain of diphtheria toxin at a first pH and release it at a second and lower pH found within endosomes;

c) selecting an antibody or antibody fragment to provide a second portion which binds said first endosomally active domain of the diphtheria toxin at said first pH and releases it at said second and lower pH; and d) constructing a hybrid reagent containing said first portion and said second portion.

6. A method for delivering functional domains of diphtheria toxin to a cellular target within the cells of a host, comprising:

a) administering to said host a hybrid reagent which has a first portion that binds to a surface of said cells and a second portion that is reversibly band to a first endosomally active domain of diphtheria toxin, wherein said first portion is joined to said second portion; and b) co-administering to said host a second hybrid reagent which has a first portion that binds to a surface of said cells and a second portion that is reversibly bound to a second endosomally active domain of diphtheria toxin; wherein the hybrid reagent is not joined to the second endosomally active domain and the second hybrid reagent is not joined to the first endosomally active domain whereby said first hybrid reagent and said second hybrid reagent bind to the surface of said cells, and are endocytosed in the same endosome into said cells, wherein said first endosomally active domain of the diphtheria toxin is released from said second portion of the first hybrid reagent, said second endosomally active domain of the diphtheria toxin is released from the second portion of the second hybrid reagent and said second endosomally active domain cooperates with said first endosomally active domain of the diphtheria toxin to form active diphtheria toxin resulting in delivery of said cytotoxic domain into the cellular target within said cells.

7. The method of claim 6 wherein the first endosomally active domain is the C domain of diphtheria toxin and the second endosomally active domain is the T domain of diphtheria toxin.

8. The method of claim 7 wherein the C domain of the diphtheria toxin is selected from the group consisting of: $C_{1-190}$ and $C_{1-193}$.

9. The method of claim 7 further comprising the T domain of diphtheria toxin in which cysteine at amino acid 201 is replaced with a non-sulfhydryl amino acid.

10. The method of claim 6 wherein the first portion binds to a cell surface receptor.

11. The method of claim 6 wherein the cellular surface which the first hybrid reagent binds to is different from the cellular surface the second hybrid reagent binds to.

12. The method of claim 6 further comprising the steps of:

a) providing a first portion of a first hybrid reagent which, upon administration to the host at a first pH, binds to the surface of said cells with the subsequent pinching off of the surface of said cells to form endosomes having a second and lower pH and containing said first hybrid reagent whereby the hybrid reagent is transported to the interior of said cells by endocytosis;

b) screening antibodies or antibody fragments which bind all or a functional portion of C domain of diphtheria toxin to determine which of said antibodies or antibody fragments bind said C domain of diphtheria toxin at a first pH and release it at a second and lower pH found within endosomes;

c) selecting an antibody or antibody fragment to provide a second portion which binds said C domain of the diphtheria toxin at said first pH and releases it at said second and lower pH;

d) constructing a first hybrid reagent containing said first portion of (a) and said second portion of (c);

e) providing a first portion of a second hybrid reagent which, upon administration to the host at a first pH, binds to the surface of said cells with the subsequent pinching off of the surface of said cells to form endosomes having a second and lower pH and containing said second hybrid reagent whereby the hybrid reagent is transported to the interior of said cells by endocytosis;

f) screening antibodies or antibody fragments which bind all or a functional portion of the T domain of diphtheria toxin to determine which of said antibodies or antibody fragments bind said T domain of diphtheria toxin at a first pH and release it at a second and lower pH found within endosomes;

g) selecting an antibody or antibody fragment to provide a second portion of the second hybrid reagent which binds said T domain of the diphtheria toxin at said first pH and releases it at said second and lower pH; and h) constructing a second hybrid reagent containing said first portion of (f) and said second portion of (g).

13. A method of killing cells by delivering functional domains of diphtheria toxin to a cellular target within the cells of a host, comprising:

a) administering to said host a hybrid reagent which has a first portion that binds to a surface of said cells and a second portion that is reversibly bound to a first endosomally active domain of diphtheria toxin, wherein said first portion is joined to said second portion; and b) co-administering to said host a free second reagent comprising a second endosomally active domain of diphtheria toxin coupled to a receptor domain of diphtheria toxin;

wherein the hybrid reagent is not joined to the second endosomally active domain and the second reagent is not joined to the first endosomally active domain whereby said hybrid reagent binds to the cell surface of said cells and said second endosomally active domain coupled to the receptor domain of the diphtheria toxin binds to diphtheria toxin receptors on the cell surface, and are endocytosed in the same endosome into said cells, wherein said first endosomally active domain of the diphtheria toxin is released from said second portion of the hybrid molecule and cooperates with the second endosomally active domain of diphtheria toxin to form active diphtheria toxin resulting in delivery of said endosomally active domains of the diphtheria toxin to the cellular target within said cells wherein said cells are killed.

14. The method of claim 13 wherein the first endosomally active domain is the C domain of diphtheria toxin and the second endosomally active domain is the T domain of diphtheria toxin.

15. The method of claim 14 wherein the C domain of the diphtheria toxin is selected from the group consisting of: $C_{1-190}$ and $C_{1-193}$.

16. The method of claim 14 further comprising the T domain of diphtheria toxin in which cysteine at amino acid 201 is replaced with a non-sulfhydryl amino acid.

17. The method of claim 13 wherein the first portion binds to a cell surface receptor.

* * * * *